(12) United States Patent
Riley et al.

(10) Patent No.: US 12,376,783 B2
(45) Date of Patent: Aug. 5, 2025

(54) APPARATUS OF INTRACRANIAL IMAGING

(71) Applicant: ArcheOptix Biomedical Inc., Kingston (CA)

(72) Inventors: Jason David Richard Riley, Kingston (CA); Vinay Kumar Singh, Kingston (CA)

(73) Assignee: ArcheOptix Biomedical Inc., Kingston (CA)

( * ) Notice: Subject to any disclaimer, the term of this patent is extended or adjusted under 35 U.S.C. 154(b) by 6 days.

(21) Appl. No.: 17/510,334

(22) Filed: Oct. 25, 2021

(65) Prior Publication Data

US 2022/0061739 A1 Mar. 3, 2022

Related U.S. Application Data

(63) Continuation of application No. 15/036,581, filed as application No. PCT/CA2014/051086 on Nov. 12, 2014, now abandoned.
(Continued)

(51) Int. Cl.
*A61B 5/00* (2006.01)
*A61B 5/055* (2006.01)
(Continued)

(52) U.S. Cl.
CPC .......... *A61B 5/4064* (2013.01); *A61B 5/0037* (2013.01); *A61B 5/0042* (2013.01); *A61B 5/0059* (2013.01); *A61B 5/0073* (2013.01); *A61B 5/055* (2013.01); *A61B 5/1077* (2013.01); *A61B 5/6841* (2013.01);
(Continued)

(58) Field of Classification Search
CPC ... A61B 5/4064; A61B 5/0075; A61B 5/0037; A61B 5/0042; A61B 5/0059; A61B 5/0073; A61B 5/055; A61B 5/1077; A61B 5/6841; A61B 5/7246; A61B 5/742; A61B 5/1079; A61B 34/10; A61B 34/20; A61B 2034/2046; A61B 2034/2048; A61B 5/725; A61B 2562/0233; A61B 2562/0242
See application file for complete search history.

(56) References Cited

U.S. PATENT DOCUMENTS 6,424,597 B1 * 7/2002 Bolomey ............. G01N 29/262
  367/128
8,954,133 B1 * 2/2015 Hanlon ................ A61B 5/0075
  600/475
(Continued)

*Primary Examiner* — Chao Sheng
(74) *Attorney, Agent, or Firm* — Porter Wright Morris & Arthur LLP

(57) ABSTRACT

The present invention provides an apparatus and method for detecting and predicting shape and underlying object properties. In accordance with an aspect of the present disclosure, there is provided an imaging apparatus having: an array of at least three co-planar electromagnetic transceiver defining a receiving plane; at least one deformable electromagnetic transceiver moveable orthogonally to the receiving plane; a two dimensional (2D) position tracking device configured to track a position of the electromagnetic transceiver on a surface 110 bounding a volume to be imaged; wherein the electromagnetic transceivers are configured to generate data from at least three depths below the surface for use in creating an image of the volume when the apparatus is moved along the surface.

9 Claims, 6 Drawing Sheets

Related U.S. Application Data

(60) Provisional application No. 61/904,559, filed on Nov. 15, 2013.

(51) Int. Cl.
  *A61B 5/107* (2006.01)
  *A61B 34/10* (2016.01)
  *A61B 34/20* (2016.01)

(52) U.S. Cl.
  CPC ............ *A61B 5/7246* (2013.01); *A61B 5/725* (2013.01); *A61B 5/742* (2013.01); *A61B 34/10* (2016.02); *A61B 34/20* (2016.02); *A61B 5/1079* (2013.01); *A61B 2034/2046* (2016.02); *A61B 2034/2048* (2016.02); *A61B 2562/0233* (2013.01); *A61B 2562/0242* (2013.01)

(56) References Cited

U.S. PATENT DOCUMENTS

| | | | |
|---|---|---|---|
| 2008/0177163 A1* | 7/2008 | Wang | A61B 5/4064 382/128 |
| 2013/0150726 A1* | 6/2013 | Riley | A61B 5/02042 600/473 |
| 2013/0169759 A1* | 7/2013 | Godavarty | A61B 5/0091 348/47 |

* cited by examiner

APPARATUS OF INTRACRANIAL IMAGING

CROSS-REFERENCE TO RELATED APPLICATIONS

This application is a continuation of U.S. patent application Ser. No. 15/036,581 filed on May 13, 2016, which is a national stage of international application number PCT/CA2014/051086 filed on Nov. 12, 2014, which claims the priority benefit of U.S. Provisional Patent Application No. 61/904,559 filed on Nov. 15, 2013, the disclosures of which are expressly incorporated herein in their entireties by reference.

FIELD

This application relates to methods, devices and apparatuses for imaging, particularly for tomographic imaging, more particularly for detecting and imaging hematomas.

BACKGROUND

The standard of care for detecting and imaging hematomas in traumatic head injury is either computed tomography (CT) or magnetic resonance imaging (MRI). Acute hematomas represent the largest cause of death from head injury, with a mortality rate of 50-60%. Mortality rate can be lowered by diagnosis and treatment within the "golden hour" following traumatic head injury. However, CT and MRI are downstream technologies employed at large medical centers; accordingly, the time from injury to diagnosis is usually at least an hour, followed by subsequent treatment outside of the golden hour. A secondary concern is the increasing belief that the number of CT scans in general needs to be reduced, particularly in pediatric populations, to reduce radiation exposure. Repeated CT is the method of choice to monitor chronic hematoma, which is a common form of Traumatic Brain Injury (TBI) in the pediatric population.

There are also existing imaging technologies that utilize the Near Infra-Red (NIR) spectrum; examples are described in WO 2006/121833 and WO 2011/084480. The former is an older approach which cannot handle full head sampling and bilateral injuries; this is problematic, since approximately 20% of hematomas are bilateral. The latter is a technique which can provide rudimentary surface maps of hematomas; however, it lacks true 3D capabilities and further has no technology to ensure full coverage, relying purely on the training of the user to guarantee coverage, which is a slow and subjective approach. Thus, the prior art NIR approaches have at least three deficits that need to be addressed: [0004] 1. Objective complete coverage by the untrained user. Neither of the aforementioned prior art devices objectively guarantees that full coverage can be obtained as in a CT/MRI. [0005] 2. Providing localization of the hematoma in the event of extra-cranial bleeding. The aforementioned prior art provides a 'pseudo-volumetric image' by comparing images acquired at two depths; however, this approach fails in the presence of a multi-layered event created by, for example, an extra-cranial bleed. If (as is often the case) there is an extra-cranial bleed associated with the intra-cranial hematoma, the extra-cranial bleed induces absorption in the surface event at depth 1 and will create uncertainty about the location and extent of the intra-cranial bleed observed at depth 2. [0006] 3. Chronic monitoring. Chronic bleeds are often continuously monitored to check for evolution of the bleed. With CT, there is a balance between how often to image to ensure patient safety vs. the radiation risks of multiple exposures. Although an NIR device obviates the radiation risk and provides a better way to study the evolution of a bleed, chronic monitoring is not possible with the aforementioned technologies because only the extent (2D) of the bleed can be monitored.

There is a need for new technology for early detection of hematomas. Such new technology would desirably permit rapid diagnosis, be portable (e.g. handheld), inexpensive, and capable of diagnosing acute injuries as well as monitoring chronic injuries with reduced radiation exposure to patients as compared with conventional CT and MRI technologies. It would be further desirable that such new technology would permit volumetric (3D) imaging in order to conduct full head sampling and observe both hemispheres of the brain at the same time for bilateral head injuries.

This background information is provided to reveal information believed by the applicant to be of possible relevance to the present disclosure. No admission is necessarily intended, nor should be construed, that any of the preceding information constitutes prior art against the present disclosure.

BRIEF SUMMARY

An object of the present disclosure is to provide an apparatus and method for detecting and predicting shape and underlying object properties. In accordance with an aspect of the present disclosure, there is provided an imaging apparatus having: an array of at least three co-planar electromagnetic transceiver defining a receiving plane; at least one deformable electromagnetic transceiver moveable orthogonally to the receiving plane; a two dimensional (2D) position tracking device configured to track a position of the electromagnetic transceiver on a surface bounding a volume to be imaged; wherein the electromagnetic transceivers are configured to generate data from at least three depths below the surface for use in creating an image of the volume when the apparatus is moved along the surface.

In accordance with another aspect of the present disclosure, there is provided an imaging apparatus for a curved surface having: an array of at least three co-planar points defining a receiving plane; a two dimensional (2D) position tracking device configured to track a position of the device on a surface bounding a volume to be imaged; and wherein the apparatus is configured to measure the curved surface using a pre-determined curved surface measuring means to measure deformation of the position tracking device.

In accordance with yet another aspect of the present disclosure, there is provided a method of intracranial imaging having: providing an imaging apparatus configured for movement along a surface of a cranium to be imaged, the imaging apparatus configured to generate data from at least three depths below the surface for use in creating an image of an intracranial volume; comparing the optical density of the at least three layers to determine an optical density ratio between the layers; and, monitoring for changes in optical density ratio as a function of time or distance moved by the imaging apparatus along the cranium.

In accordance with yet another aspect of the present disclosure, a method of intracranial imaging having: providing an imaging apparatus moving along at least three co-planar points defining a receiving plane, and implementing a two dimensional (2D) position tracking device configured to track a position of the device on a surface bounding a volume to be imaged, and wherein the apparatus is configured to measure the curved surface using a pre-determined curved surface measuring means to measure deformation of the position tracking device; comparing the optical density ratio of the surface based on the curved surface means to measure deformation; and monitoring for changes in optical density ratio as a function of time or distance moved by the imaging apparatus along the cranium.

According to an aspect of the present disclosure, there is provided an imaging apparatus comprising: an array of at least three co-planar electromagnetic transceivers defining a receiving plane; at least one deformable electromagnetic emitter moveable orthogonally to the receiving plane; a two dimensional (2D) position tracking device configured to track a position of the electromagnetic emitter on a surface bounding a volume to be imaged; wherein the electromagnetic emitter and transceivers are configured to generate data from at least three depths below the surface for use in creating an image of the volume when the apparatus is moved along the surface.

The surface may be curved. In these instances a curved surface measuring means may be utilized for measurement of the curved surface. The curved surface measuring means may be implemented in a variety of ways as long as the method/mechanism allows for accurate measurement of the curved surface.

In at least one embodiment, the curved surface measuring means include obtaining the image by continuously re-aligning the data from two dimensional (Cartesian) co-ordinates into curvilinear co-ordinates. The apparatus may further comprise a first gyroscope and a second gyroscope spaced apart from the first gyroscope in a direction orthogonal to the receiving plane by a known distance. The apparatus may further comprises a displacement sensor configured to measure deformation of the at least one deformable electromagnetic emitter moving on the surface. The apparatus may further comprise a removable component containing at least the electromagnetic emitter and electromagnetic transceivers. This permits use of the apparatus with multiple interchangeable removable components, each removable component comprising a different spacing between the electromagnetic transceivers and/or between the electromagnetic transceivers and the electromagnetic emitter. In the case of medical imaging, selection of a particular removable component may be based upon the age, gender or ethnicity of a subject being imaged. The removable component may comprise an opaque exterior housing, with the electromagnetic transceivers and electromagnetic emitter operable inside the housing. The electromagnetic emitter may comprise an optical emitter (such as a near infra-red [NIR] emitter) and the electromagnetic transceivers may comprise optical transceivers (such as NIR transceivers). The optical emitter may comprise a light emitting diode (LED) and the optical transceivers may comprise light receiving diodes (LRD) or avalanche photo-diodes (APD). The apparatus may be configured to utilize multiple optical wavelengths and may be configured to utilize a temporal multiplexer and/or band pass filter to prevent contamination between the wavelengths.

In at least one embodiment, two or more gyroscopes are utilized for enhanced performance with respect to measuring a curved surface of a subject.

An imaging system according to the present disclosure may comprise an imagine device as previously described interconnected with a computer configured to display a three-dimensional (3D) image of the volume being imaged.

The imaging apparatus as previously described may be used for intracranial imaging for the detection and/or monitoring of a sub-dural or epidural hematoma of a subject.

According to another aspect of the present disclosure, there is provided a method of intracranial imaging comprising: providing a near infra-red (NIR) imaging apparatus configured for movement along a surface of a cranium to be imaged, the imaging apparatus configured to generate data from at least three depths below the surface for use in creating an image of an intracranial volume; comparing the optical density of the at least three layers to determine an optical density ratio between the layers; and, monitoring for changes in optical density ratio as a function of time or distance moved by the imaging apparatus along the cranium.

The method may further comprise adjusting the number of layers being imaged in response to a change in the optical density ratio. The method may further comprise adjusting the rate of movement of the imaging apparatus along the cranial surface in response to a change in the optical density ratio. The method may further comprise comparing features of the image with a brain atlas to obtain a registered image location within the cranium. The method may further comprise creating a preferred path for the imaging device based on the registered image location and the brain atlas. The method may further comprise placing a head gear that is transparent to NIR electromagnetic radiation on the cranium and indicating the preferred path on the head gear. The preferred path may be indicated with reference to electromagnetic reference signals of the head gear that interact with the imaging device to indicate its position on the head gear or by optically detectable reference indicia on the head gear.

The present disclosure provides advanced shape tracking and predictive shape navigation with multi layered imaging capacity for real-time tomographic reconstruction of structural contrast. The present disclosure provides an approach to imaging that permits creation of true tomographic images with objectively guaranteed coverage. These shape extraction and predictive tracking models have further applications to a multitude of medical technologies. They are especially relevant in the current drive to the development of 'tricorder like' technologies.

The present disclosure is also useful for any implementation where surface reconstruction is required using a surface scanning technology, either purely for surface retrieval—with applications from art studies (e.g. contact shape and texture copying) to exploration technologies (e.g. wreck exploration)—or for any studying environment where scanning is occurring and the need to know the structure of the scan is important as well the data scanned (e.g. scanning a pipeline for material defects or damage).

The present disclosure is also useful for any volumetric imaging that can be achieved by some form of contrast imaging or 'shadow casting' can be implemented with the present disclosure; for example, looking for impurities in a neutron reactor. Predictive tracking is an even broader area of application. Some applications include: medical scanning from small handheld technologies passed over the body ensuring objective full coverage; exploring a wreck remotely where, given a ship's layout, a drone could guide itself over the whole vessel checking the surface for weaknesses and stresses that may be risks to divers; remote surveying; tracking for exploring mineral deposits underground; space rovers and so forth.

The layered structural imaging in real time also has multiple uses in medical imaging using NIR. Such uses include, for example, obtaining better models for any structural studies currently done using sophisticated algorithms with static devices with limited sampling. These include, but are not limited to, stroke studies and breast cancer studies.

Uses may be extended to volumetric spectroscopic imaging at multiple scales and multiple wavelengths.

One application of the technology is in the detection and imaging of hematomas. The present disclosure is useful in acute and chronic, sub and epidural hematoma detection and imaging for triage. The present disclosure uses multiple depths of sensory paths to recover a layered structural image of the medium. The present disclosure includes advanced mathematical techniques to capture shape and uses a priori atlases to guide and determine the path of tracking/measurement. An objective design is provided to ensure coverage of the full head based on advanced shape tracking models and predictive motion guidance systems.

In another medical embodiment, the present disclosure may be used to measure concussions due to potential physiological changes induced in the event. There is some suggestion that concussion induces a change in the volume of cerebrospinal fluid. The present disclosure may be adapted to detect near cranial surface changes in cerebrospinal fluid. As such, a concussion detection system may be provided.

Recent literature in the art has shown that near surface changes in thickness of the cerebro-spinal fluid relates to the presence of a concussion. By using multiple NIR sensors over a known curvature we can detect the thickness and depth of the CSF by way of shape descriptors obtained from the intensity profile across the surface. By tracking this in motion across a known shape one may create a map of CSF thickness in this region. This information will provide a map of the CSF beneath the skull, and will provide information on abnormal thickening which would indicate the presence of a concussion.

In another medical embodiment, biological markers have been identified whose presence in the CSF indicate a negative response to the "return to play" question. The absence of said markers allow for a "return to play" (or combat, or remove the flag for a state of heightened risk from further head injury). It is possible to tag said markers using known antibodies or affibodies tagged with an imaging marker. Such markers would be detectable using such an apparatus and map-able over the head.

The use of multi-layered devices to address true volumetric as opposed to pseudo-volumetric images is a significant improvement over the two-layered device of WO 2011/084480. Further, the present disclosure abandons the requirement for multiple wavelengths without sacrificing utility, which is significant in an effort to simplify the technology to its basic need. This allows use of practically any NIR wavelength, thereby simplifying the detection system by making the detection system wavelength independent.

The present disclosure may provide any one or more of the following advantages: 1. Objective complete coverage by the untrained user. The present disclosure permits obtaining full coverage as in a pre-existing structural image (e.g., CT and MRI, and the like), where it is objectively guaranteed. With the new atlas guided tracking system, an objectively guaranteed objective coverage using a miniaturized scanning imaging device is provided. 2. Providing localization of the hematoma in the event of extra-cranial bleeding. By applying a multi-layered model a layered volumetric image may be recovered fully, allowing discrimination of the possibility of an intracranial bleed beneath an extra-cranial bleed. In order to acquire better sensitivity and specificity the present disclosure adds extra layers of information to provide higher sensitivity, with specificity following from this. 3. Chronic monitoring. The use of multiple layers permits study of the true 3D (extent and thickness) evolution of the bleed as regularly as needed without irradiation risk. This is significant since the depth information is important, providing information about how much the hematoma is impinging on the brain. 4. Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

Embodiments of the present disclosure will be better understood in connection with the following Figures, in which.

DETAILED DESCRIPTION

Definitions

Figure 1:
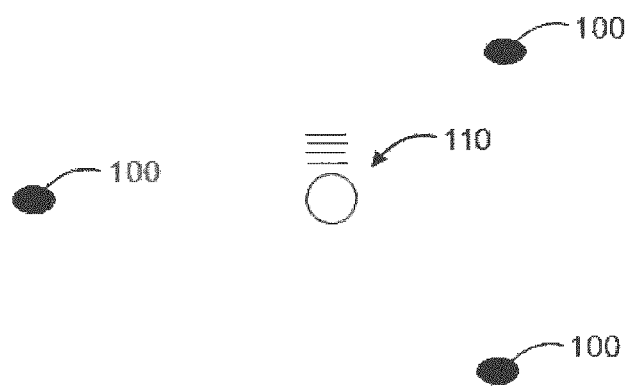
FIG. 1 schematically illustrates intended geometry of a tracking head for a shape recovery/tracking sensor system for a device of the present disclosure in which the configuration is designed to achieve a four point geometry intended to give a 3D reference position.

The instant disclosure is most clearly understood with reference to the following definitions:

Unilateral hematoma shall be understood to mean a hematoma inside the head and in which blood collection or accumulation takes place on one side of the head.

Bilateral hematoma shall be understood to mean a hematoma inside the head and in which blood collection or accumulation takes place on both sides of the head.

An epidural hematoma shall be understood to mean a hematoma inside the head and where the blood collects or accumulates outside the brain and its fibrous covering (the Dura), but under the skull.

A subdural hematoma (SDH) shall be understood to mean a hematoma inside the head and where the blood collects or accumulates between the brain and its Dura.

An intracerebral hematoma shall be understood to mean a hematoma inside the head and where the blood collects or accumulates in the brain tissue.

A subarachnoid hematoma or hemorrhage (SAH) shall be understood to mean a hematoma inside the head and where the blood collects or accumulates around the surfaces of the brain, between the Dura and arachnoid membranes. The term patient shall be understood to include mammalians including human beings as well as other members of the animal kingdom.

An Extra Cranial Bleed shall refer to any accumulation of blood outside the cranium (skull) of the patient.

An Intra Cranial Bleed shall refer to any accumulation of blood inside the cranium (skull) of the patient. It shall include, but not be exclusively: epidural, subdural, unilateral and bilateral hematomas, also included will be intracerebral hematomas.

An Acute Hematoma shall refer to the medical condition of a rapidly evolving bleed requiring immediate treatment.

A Chronic Hematoma shall refer to the medical condition where the hematoma is small and evolving over time, requiring inpatient care and assessment over extended periods (multiple imaging cycles) to assess treatment needs.

Unless defined otherwise, all technical and scientific terms used herein have the same meaning as commonly understood by one of ordinary skill in the art to which this present disclosure belongs.

Embodiments

Two primary embodiments are described herein, although the methods, devices and apparatuses described generally herein have a broad range of applications and lend themselves to many additional embodiments. Further, components of the present disclosure may be applied either individually or as a whole to other applications.

In the first embodiment, a portable imaging device is provided for detection of hematoma. This device uses a multi-layered (3 or more) model and circuitry and algorithms designed to discriminate different depths within the head and identify any 'concealed intracranial bleed'. This device is provided in a version with a guidance system and a version without a guidance system. The device may also include multiple interchangeable detection heads to accommodate different skull thicknesses, which may vary according to age, race and gender.

In the second embodiment, an imaging device is provided and connected with a computing apparatus. In the second embodiment, a greater number of layers are employed to create more complete volumetric images of the hematoma for use in, for example, research or surgical guidance. The second embodiment may employ a portable imaging device according to the first embodiment as a detector that is equipped with an appropriate detection head and interfaced by wireless or wired connection to the computer apparatus. Alternatively, the imaging device of the second embodiment may be purpose built for greater sensitivity and/or field of view. For chronic monitoring applications, the second embodiment may include a stand, helmet or similar support structure to assist in positioning the imaging device proximal to the patient's head for a prolonged period of time.

Decoupling Motion from Shape

The prior art in the field of shape reconstruction and remote sensing applications (where an object's geometry is recovered) relies upon data collected at a distance, using fixed position sensor readings obtained from multiple sensors of known location applied to a static target. In the present disclosure, data must be collected from tracking points proximate a target using a single light source that is not at a fixed location, with the sensor placed upon a living target (i.e. potentially moving). This provides an entirely different problem. Current solutions involve the use of fixed observation points monitoring the moving measurement device (stereotaxic imaging), or using a single gyroscopic measure to monitor the motion of the device and recover its path and orientation. These fall short if the target object is moving. This provides a problem in terms of decoupling the motion of the device caused by the moving target from the spatial information collected as the imaging device moves over the target.

The present disclosure employs two approaches to overcome these problems. The approaches are based upon the premise that, given a surface that is inherently 2D, a tracker (e.g. a mouse tracker) may be used to describe changes in location of the tracker on the surface; however the X-Y coordinate system will be non-unique and may be distorted by curvature. Despite this, local differential changes may be examined and converted to accurate surface translations if the local curvature of the object is understood.

A first technique for accomplishing this is based on using two gyroscopes placed at known distances from the X-Y measure to permit decoupling of the yaw of the device due to target shape from the yaw due to target motion.

A second technique measures the deflection of a sensor caused by the shape of the object if it is mounted at a known point inside a fixed three point geometry. This provides a known tetrahedron with a known Great sphere that will fit the four apexes. This provides a direct way to measure shape change by decoupling the motion of the target from the measurement.

Shape Recovery

Using standard algorithms, if the motion of an object is tracked in a fixed 3D frame, the object's location and path may be described and a shape based on this trajectory may be generated. However, if the 3D frame is also moving, it is more difficult to determine the object's path and generate a shape, because it is difficult to separate motion of the object from motion of the tracking device. In one aspect of the present disclosure, an approach to handling this problem is provided. It can be shown mathematically that any closed surface object (or part thereof) is uniquely described by its surface normal and surface location in 2D. To measure this, a device such as a mouse tracker is first used to acquire 2D lateralisation and continuously transformed as the mouse travels based on the Jacobian of transformation to continuously realign these changes to the local differential changes based on the surface topology or curvature change. Extracting this simultaneously is important. In the first instance one could use a single gyroscope, but this is susceptible to changes induced by the motion of the object and not the changes in the object itself. To avoid this, the following approaches are used.

In at least one embodiment, by using a deformable device head (similar to a razor head) with three fixed contact points (forming a tripod), a measurable, continuously variable deformation is created at the centre of this deformable surface. If the deformation is measured (by any method including, but not limited to, a laser rangefinder or a spring based deformation calibration) the local 'Great Sphere' generated by this deformation may be extracted from trigonometric relations. This provides the local curvature of the surface. As the device is moved and the curvature changes, shape information is obtained which is completed by x-y tracking at the same location. This configuration is illustrated in FIG. 1 and FIG. 2. As stated above, the x-y data needs to be recalibrated to .theta..phi. (or similar curvilinear coordinates) based on the Jacobian of transformation, as they are not equivalent to latitude and longitude when measured using a conventional sensor. In at least one embodiment, the utilization of a deformable device head comprises a curved surface measuring means.

Referring to FIG. 1 and FIG. 2, FIG. 1 illustrates the intended geometry of the tracking head. The configuration is designed to achieve a four point geometry intended to give a 3D reference position. Three fixed points are given by the corners 100 of the device chassis, or by other fixed structures incorporated in other embodiments. These form the base of a tetrahedron that will be described below with reference to FIG. 2. The fourth point is a deformable sensor 110 that deforms orthogonally to the plane of the three fixed points; in the current embodiment, the forth point is situated at the circumcenter of the triangle of points. This position is chosen solely for the ease of the mathematics and other non-centrally located embodiments may also be used, but would require more extensive mathematical models to resolve the 3D shape.

Figure 2A:
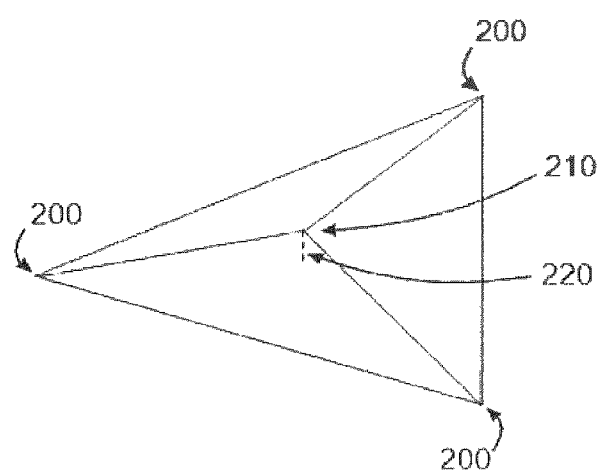
FIG. 2A schematically illustrates the concept of recovery of curvature from a deformation applied to a shape recovery/tracking sensor system for a device of the present disclosure, where the formation of a measured tetrahedral is illustrated.
Figure 2B:
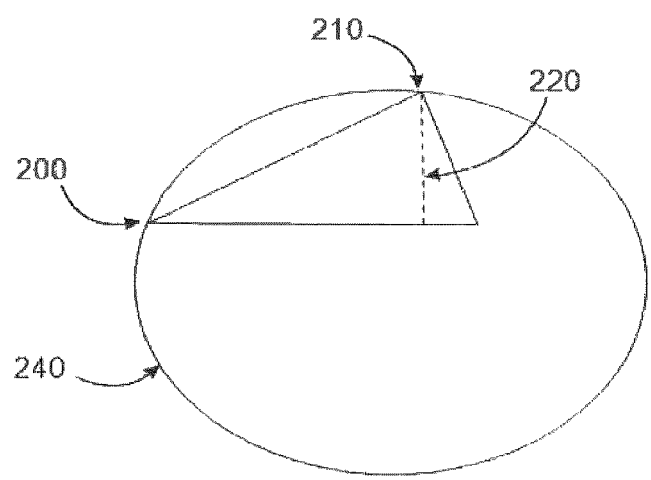
FIG. 2B illustrates the calculable fitted sphere constrained by the measured height of the measured tetrahedral of FIG. 2A.

FIG. 2A and FIG. 2B illustrate the concept of recovery of curvature from a deformation, where FIG. 2A shows the formation of a measured tetrahedral and FIG. 2B shows the calculable fitted sphere constrained by the measured height. FIG. 2A shows how a tetrahedron is formed when deformable sensor 110 moves away from the plane created by fixed points 200 at the corners 100 of the device chassis. The deformation gives the tetrahedron a measured height 220. The design of this is such that the 'largest sphere' that sits on all points of the tetrahedron can be detected, giving us a measure of curvature at deformable point 210, which is the location of the deformable sensor 110 out of the plane defined by the fixed points 200. FIG. 2B illustrates the great circle 240 of the sphere passing through deformable point 210 and one apex of the triangle created by one of the fixed anchor points 200. If the triangle is equilateral this is identical to all three points, making the math simpler, although other configurations are possible with more complex mathematics. In this instance we may derive from the geometry of the triangle and the height 220 of the tetrahedron the radius of this great circle 240, equivalent to the radius of the sphere. This gives a local measure of curvature. As the device is translated around, this curvature will change giving the local shape, along with a measure of the .delta.x and .delta.y provided by a collocated tracking device (either a mouse tracker or similar). It is envisaged that the deformation sensor would work off the 'back' of the motion tracking device, with zero being set as the depth of the tracking unit. Using spherical coordinates, or other mathematical corrections, .delta.x and .delta.y can be translated into angular components of shift giving true surface motion. As the curvature is constantly updated, the location may be modified based on the combined data.

Figure 3:
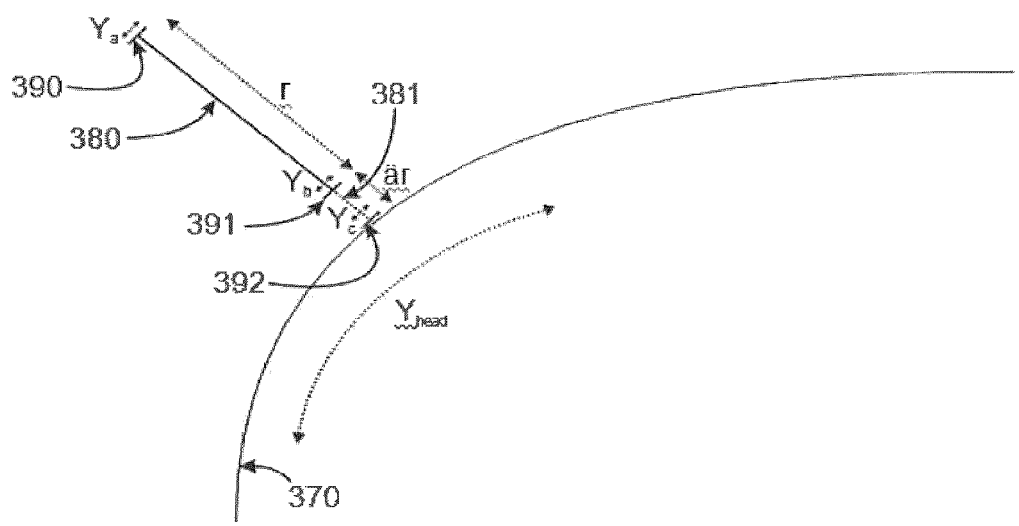
FIG. 3 schematically illustrates use of two gyroscopes on a stem separated by distance r with b being a distance delta r from a third motion sensor (e.g. a surface tracker) in a shape recovery/tracking sensor system for a device of the present disclosure.

With reference to FIG. 3, in a second approach, two gyroscopes 390 and 391 may be used at fixed positions (distances) from an x-y motion tracker 392. Using trigonometric relations it may be established that the two gyroscopes' movements come from the motion relative to a surface 370 and the motion of the surface 370. By having the local distance of travel, the vectors of translation may be computed and global movement may be separated from local movement, thereby returning a shape. A changing surface normal 6n is generated, which permits regeneration of the great circle, from where it is possible to proceed as outlined above. FIG. 3 illustrates the two gyroscopes 390 and 391 on a stem separated by distance r along a tracking device axis 380 with gyroscope 391 being a distance Sr from the x-y motion tracker 392 (e.g. a surface tracker) along a deformable component 381 of the device axis 380. The quantity of interest is the angular change in the gyroscope positions as a head of the motion tracker 392 moves in a yaw Y.sub.c. However a further yaw Y.sub.head will be introduced by the motion of the head so the angular component will have to be extracted from the relative yaws Y.sub.a and Y.sub.b of the two fixed positions and the x-y component tracked by the distance moved at the head. This may be done by assuming .delta.r>>r and therefore negligible, or by measuring it and giving a recursive algorithm to eliminate Y.sub.head.

Shape Tracking (Prediction)

It is commonly known that one may register a volumetric image of any individual's head to an atlas head based on a variety of techniques. It is in fact a much simpler task to map one surface to another, in a similar way that image warping is achieved between two faces. If a shape is being generated as the scanning device travels, as described previously, the generated shape may then be mapped to a predicted atlas shape (e.g. a head, pipeline, room configuration). As tracking continues, an increased data (larger shape), is obtained, which permits improvement in the prediction of where the scanning device is located, in a similar fashion as a Kahlman filter. This is a novel approach to updating registration based on partial data extraction. Having done this, the position of the scanning device may be predicted, as it is now possible to register the image as it is taken and use this as a guide to where the scanning device needs to go next, for example via a user interface screen with an image of the atlas with a 'tracking path' on it showing where the scanning device is and where it is traveling, leaving the user then to 'follow' the path. Alternatively, in some remote applications, a guidance software and associated motor hardware are included to allow the device to move itself.

Layered Imaging

A layered image is generated by providing ratiometric measurements from one depth to another. To achieve maximum accuracy, it is possible to provide a set of measures by combining variation of ratios. For example, one could generate a simple (naive) image by comparing one depth to all others. However, the present disclosure allows more sophisticated images to be generated by comparing each depth to its predecessor, or by skipping 'n' (where n is some number) depths. By using combinatorial logic of different ratios, the best (sharpest) images are provided. One must further appreciate that 'best' will be application dependent, so the methodology is described herein in its most generic form.

Specifically, in terms of targeting the extra-cranial bleeds and detecting "hidden intra-cranial bleeds", the sudden change in all channels caused by an extra-cranial bleed allows the imaging device to 'switch mode' from a simple approach of looking at the local vs. global ratios to including a quasi-local to local ratio based on the multiple depths as a normalising factor to detect the presence of blood-skull-blood. The exact methodology may depend upon one or more of race, gender and age, due to the associated variation in skull thickness. This technique allows one to regenerate background averages and determine the presence/absence of a non-blood layer sandwiched between the two blood layers based on ratiometric comparison.

Figure 4:
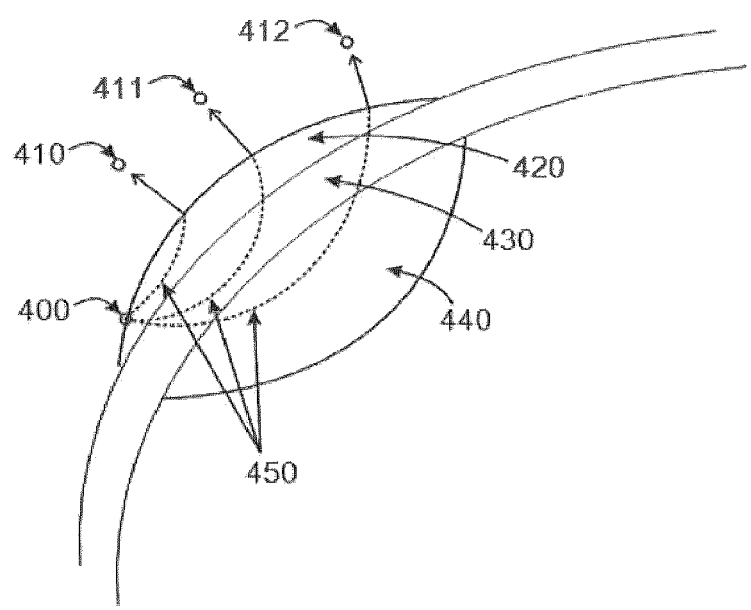
FIG. 4 schematically illustrates how to differentiate between extra-cranial and intra-cranial bleeds by identifying a skull/scalp layer between the two bleeds using extra penetration depths provided by a multi-layered NIR array sensor system in accordance with the present disclosure; and, FIG. 5 schematically illustrates a multi-layered NIR array sensor system for a device in accordance with the present disclosure to implement the differentiation illustrated in FIG. 4.

The multi-layered principle of this device, in its simplest implementation (3 sensory depths) is illustrated in FIG. 4. FIG. 4 illustrates how, by probing multiple depths, layered structure may be recovered; for example, in the case of an extra-cranial bleeding covering an intracranial injury. In the presence of an extracranial bleed 420, prior art methods and devices are unable to make decisive comment on the presence of an intracranial bleed 440. For example, the device described in WO 2006-121833 will simply detect the presence or absence of blood and the extracranial bleed will cause an automatic positive. The device described in WO 2011/084480 will produce unknown data and it will be unable to provide a definitive answer as to whether or not the image is confounded by an extra-cranial bleed. In contrast, the device of the present disclosure uses at least 3 depths to differentiate a multi-layered model, thereby permitting separation of the extra and intra cranial bleeds by identifying a skull/scalp layer 430 between them using extra penetration depth or depths. NIR paths 450 illustrated in FIG. 4 passing from a source 400 to each of detectors 410,411,412 show clearly how differentiation is achieved. The number of paths and detectors may increase beyond three, depending on the potential range of thicknesses of the extracranial bleed 420. Further embodiments of the device utilize more layers in order to see 'beneath' the intracranial bleed 440 to provide thickness information in an evolving chronic hematoma.

Physical Aspects

A device of the present disclosure has two built in sensor systems, the first being a NIR array designed to assess the underlying tissue structure, for example, and the second being a shape recovery/tracking sensor system. The former is illustrated in FIG. 4 from a functional perspective. The latter is described in detail in FIGS. 1-3.

Figure 5:
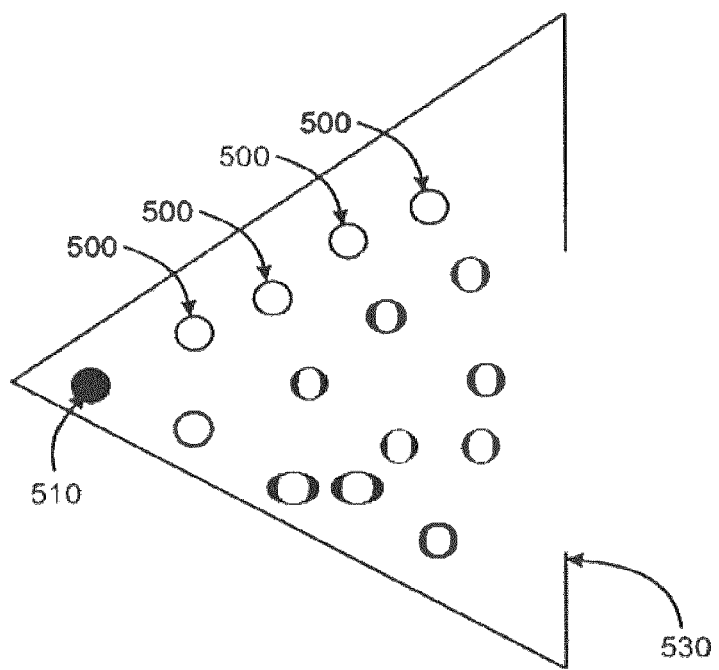

Physically, the device may employ a single light source (e.g. light emitting diodes (LED)) and an array of detectors (e.g. light receiving diodes (LRD) or avalanche photo diodes (APD)). With reference to FIG. 5, the device may be arranged such that light source 510 is placed near one apex of a triangular head 530 of the device and then an array of detectors 500 (only four of fourteen labeled) are placed at known distances from the light source 510. In FIG. 5, four banks or rows of detectors 500 (one labeled in each row) are illustrated, each row of detectors initially providing one signal. However, in other embodiments of the device the signals may be separated for advanced imaging techniques. In FIG. 5, the rows are seen vertically and to the right of the light source 510 with two detectors in the first row, three detectors in the second row, four detectors in the third row and five detectors in the fifth row.

The use of a laser mouse type motion tracker may lead to cross contamination of the sensor data, so frequency multiplexing or the use of wavelength bandpass filters to separate the light based signals may be necessary.

Given the successful layering as illustrated by FIG. 4, the question of depth penetration of the array must be considered in the present disclosure. In the prior art, the heads of the devices do not affect the geometry of the sensor array in the device. In the present disclosure, interchangeable heads are designed specifically to adjust the geometry of the sensor array to make it age, gender and ethnicity specific. In one embodiment, there are heads for two genders, two age groupings and potentially 2 or 3 primary ethnicities. The idea of depth specific configurations, based on subject, is unique to the present device in the NIR literature. To achieve depth specific configurations, a flexible set of sources and detectors that return to a resting state are provided. As the detection head of the device is applied to the patient, it collects data from each source and detector and guides it to the correct location based on the age, gender and ethnicity of the subject for which the detection head is designed. In one embodiment, the head is optically transparent at the setting for the source/detector, but elsewhere it is optically opaque to prevent light leakage. Heads desirably are sterilizable or at least include a disposable sterilizable component due to the potential of blood being present and the need for sterility of the device.

In an alternative embodiment, a diffuse optical device may be employed in which the detectors are interchangeable with the light source, and temporal or frequency modulation is used to extract the different data channels. Thus, a single detector may be used and the light source multiplexed for measurement of different layers. This is especially useful for devices for multiple layered measurements where the number of detectors would otherwise be too large for a portable device. Diffuse optical strategies thus permit the construction of smaller, less expensive devices with less cumbersome electronics.

Method of Using a Device for Diagnosis

The aim is to minimise the number of potential detection heads. The choice of detection head may rely upon whether or not the patient is adult vs. child, male vs. female and then ethnicity. Ethnic measures of skull thickness may indicate 2 possibly 3 different choices. It is possible to remove the need for detection head selection by employing greater separation distances (greater than 3). However, it may be important to have a head selection option available.

The device is applied to a head of the subject starting at a fixed point (above an ear for example). The user then spirals the device to cover the whole of the subject's head to search for any possible injury. This process provides full head coverage. To ensure full head coverage, a guidance screen may be included that informs the user how to move the device. The guidance screen may involve any suitable type of screen, for example an LCD screen (or similar) with a tracker path, a warning bar that shows the user whether they are following the prescribed path, or a combination thereof.

When used as an emergency diagnostic tool, the imaging apparatus may have an indicator light to inform the user that a hematoma is present and that the patient's care should be prioritized accordingly. The second embodiment involves the use of a secondary computer device (laptop or desktop), optionally with a wired connection, a wireless connection, or a bespoke docking unit. The computer runs software on the data collected from the imaging device to provide an image of the head giving the location of the bleed. In further embodiments, a plurality of detectors may provide a greater number and more advanced volumetric images, providing not only information on where to drill to alleviate pressure but also the option to continuously monitor the evolution of a chronic condition to allow for the determination of when surgical intervention becomes necessary.

In the case of a priori known environments, for example in medical imaging applications, a priori shape information about an object to be measured (e.g. the head of a subject) may be available to help ensure coverage of the measuring operation and shape recovery from the measurements made. In such cases, a suitable path could be pre-marked on the object and the path may be tracked to ensure coverage and shape recovery. However, it is challenging to correctly describe a suitable path on an object and then to correctly follow the path with the measuring device. To accomplish this, an inert shape fitting cover may be applied to the object being measured and a surface path marked on the cover to provide a reference for determining the position of the measuring device as it moves on the cover. A priori information from a "generic" shape of the object together with information provided about the interaction of the measuring device with the cover provides position tracking and shape reconstruction.

In one embodiment where a person's head is being scanned, an optically neutral head gear (e.g. a cap such as a 'swim cap' like attachment) may be placed on the person's head and a suitable path "marked" on the head gear. This has the added advantage of providing extra sterility and ease of use of the measuring device. The path may be "marked" in a variety of ways.

In at least one embodiment, a set of RF transmitters may be embedded in the head gear to permit continuous triangulation of the position of the measuring device on the head gear during the measuring operation. Data from the RF transmitters may be stored in the measuring device and outputted in the same manner as the optical data collected by the measuring device.

A track marked as a bar code may be applied to the head gear and some 'image' of the bar code may be stored while the measuring device is in transit. From the image of the bar code, the position of the measuring device along the track may be recovered at any time, thereby recovering the location of the measuring device.

A track with a raised tracking edge may be applied to the head gear and the measuring device hooked to the head gear via the raised edge. Position of the measuring device may be provided from images of the raised track in a way similar to the bar code, and the raised track may provide a way to ensure continuous contact of the measuring device with the person's head.

References: The contents of the entirety of each of which are incorporated by this reference. Ben Dor B, et al. (2006) System and Method for Detection of Hematoma. International Patent Publication WO 2006-121833 published Nov. 16, 2006. Riley J D, et al. (2011) Method for Detecting Hematoma, Portable Detection and Discrimination Device and Related Systems and Apparatuses. International Patent Publication WO 2011/084480 published Jul. 14, 2011.

The novel features will become apparent to those of skill in the art upon examination of the description. It should be understood, however, that the scope of the claims should not be limited by the embodiments, but should be given the broadest interpretation consistent with the wording of the claims and the specification as a whole.

What is claimed is:

1. An apparatus for detecting and monitoring intracranial fluid in a subject, the apparatus comprising:
   three fixed contact points defining a plane, each said contact point being configured to contact a curved surface bounding a volume to be imaged;
   an array of at least three co-planar electromagnetic transceivers defining a receiving plane;
   at least one deformable electromagnetic emitter moveable orthogonally to the receiving plane and the plane defined by the three fixed contact points, wherein the at least one deformable electromagnetic emitter is configured to contact the curved surface bounding the volume to be imaged;
   a two-dimensional (2D) position tracking device configured to track a position of the apparatus in x-y coordinates while moving on the curved surface bounding the volume to be imaged; and
   a displacement sensor configured to measure deformation of the at least one deformable electromagnetic emitter moving on the curved surface;
   wherein the electromagnetic emitter and transceivers are configured to generate optical density data relating to presence or absence of the intracranial fluid from at least three depths below the curved surface, wherein the optical density data is for use in creating an image of the volume as the apparatus is moved along the curved surface;
   wherein the local curvature of the curved surface is determined by orthogonal displacement of the deformable electromagnetic emitter relative to the plane defined by the three fixed contact points; and
   wherein the local curvature of the curved surface is correlated to the position of the apparatus as measured in x-y coordinates.

2. The apparatus of claim 1, wherein the apparatus is configured to output the optical density data to a computer configured to display a three-dimensional (3D) image of the volume.

3. The apparatus of claim 1, wherein the intracranial fluid is blood and the apparatus is configured for use in intracranial imaging for the detection and monitoring of a hematoma of the subject.

4. The apparatus of claim 1, wherein the intracranial fluid is cerebrospinal fluid and the apparatus is configured for use in intracranial imaging for the detection and monitoring of a concussion of the subject by generation of the optical density data relating to near cranial surface changes in cerebrospinal fluid.

5. The apparatus according to claim 1, wherein the electromagnetic transceivers are optical transceivers and the electromagnetic emitter is an optical emitter.

6. The apparatus according to claim 5, wherein the optical emitter is a near infra-red (NIR) emitter and the optical transceivers are NIR transceivers.

7. The apparatus according to claim 6, wherein the optical emitter comprises a light emitting diode (LED) and wherein the optical transceivers comprise a light receiving diode (LRD) or avalanche photo-diode (APD).

8. The apparatus according to claim 1, wherein the apparatus is configured to utilize multiple optical wavelengths.

9. The apparatus according to claim 8, wherein the apparatus is configured to utilize at least one of a temporal multiplexer, band pass filter, and frequency multiplexer to prevent contamination between the multiple optical wavelengths.

* * * * *